United States Patent [19]
Niehoff

[11] Patent Number: 5,662,612
[45] Date of Patent: Sep. 2, 1997

[54] CONTROLLING PLUNGER DRIVES FOR FLUID INJECTIONS IN ANIMALS

[75] Inventor: Kenneth J. Niehoff, Cincinnati, Ohio

[73] Assignee: Liebel Flarsheim Company, Cincinnati, Ohio

[21] Appl. No.: 494,795

[22] Filed: Jun. 26, 1995

Related U.S. Application Data

[63] Continuation of Ser. No. 157,823, Nov. 24, 1993, abandoned.

[51] Int. Cl.$^6$ ............................................. A61M 37/00
[52] U.S. Cl. .................... 604/155; 604/151; 417/15; 417/63
[58] Field of Search ..................... 604/67, 131, 151, 604/154, 155; 417/15, 33, 42, 43, 44 J, 63

[56] References Cited

U.S. PATENT DOCUMENTS

| | | | |
|---|---|---|---|
| 4,475,666 | 10/1984 | Billbrey et al. | 604/155 |
| 4,529,401 | 7/1985 | Leslie et al. | 604/155 |
| 4,685,903 | 8/1987 | Cable et al. | 604/151 |
| 4,722,734 | 2/1988 | Kolln | 604/151 |
| 4,741,732 | 5/1988 | Crankshaw et al. | 604/155 |
| 4,767,406 | 8/1988 | Wadham et al. | 604/67 |
| 4,854,324 | 8/1989 | Hirshman et al. | 604/155 |
| 4,978,335 | 12/1990 | Arthur, III . | |
| 4,988,337 | 1/1991 | Ito | 604/67 |
| 5,034,004 | 7/1991 | Crankshaw . | |
| 5,078,836 | 1/1992 | Sancoff et al. | 604/67 |
| 5,135,507 | 8/1992 | Haber et al. | 604/187 |
| 5,236,416 | 8/1993 | McDaniel et al. . | |
| 5,242,408 | 9/1993 | Jhuboo et al. | 604/67 |
| 5,256,157 | 10/1993 | Samiotes et al. | 604/67 |
| 5,342,298 | 8/1994 | Michaels et al. | 604/65 |
| 5,354,287 | 10/1994 | Wacks | 604/232 |
| 5,356,393 | 10/1994 | Haber et al. | 604/222 |
| 5,383,858 | 1/1995 | Reilly et al. | 604/152 |
| 5,425,716 | 6/1995 | Kawasaki et al. . | |

FOREIGN PATENT DOCUMENTS

| | | |
|---|---|---|
| 160 303 | 11/1985 | European Pat. Off. . |
| 164 904 | 12/1985 | European Pat. Off. . |
| 364010 | 4/1990 | European Pat. Off. ............. 604/151 |
| 482 677 | 4/1992 | European Pat. Off. . |
| 523 343 | 1/1993 | European Pat. Off. . |
| WO89/06145 | 1/1988 | WIPO . |

OTHER PUBLICATIONS

Declaration of James H. Goethel.
Declaration of Kenneth J. Niehoff.
Medrad, Inc., "The First and Only True Injection System" Medrad Mark V System Brochure, 1988.
Dwayne Crawford, "Declaration of Dwayne Crawford".
Brochure for "Angiomat 6000" of Liebel–Flarsheim, 2111 E. Galbraith Rd., Cincinnati, OH 45215, copyright 1987.
Brochure for "Angiomat CT" of Liebel–Flarsheim, 2111 E. Galbraith Rd., Cincinnati, OH 45215, copyright 1988.
Brochure for "PercuPump 1A" of E–Z–EM, Inc., 717 Main St., Westbury, NY 11590, copyright 1990.

*Primary Examiner*—Todd E. Manahan
*Attorney, Agent, or Firm*—Wood, Herron & Evans, L.L.P.

[57] ABSTRACT

A computer-controlled injector of the type as a motor which advances and retracts a plunger located within a syringe housing toward and away from a nozzle located in the front of the syringe to inject fluid into or out of an animal subject. The injector tracks the plunger position during an injection, and compensates for plunger extenders found in partially pre-filled syringes by applying a stored offset value to the computed plunger position, to produce a corrected plunger position reflecting the actual position of the plunger and compensating for the presence of the extender. The offset value can be determined by querying the operator as to the capacity of the syringe and determining therefrom the appropriate offset value, or may be automatically computed by detecting physical indicia on the syringe or extender which indicate the length of the extender.

12 Claims, 11 Drawing Sheets

CONTROLLING PLUNGER DRIVES FOR FLUID INJECTIONS IN ANIMALS

RELATED APPLICATION

This application is a continuation of application Ser. No. 08/157,823 filed Nov. 24, 1993 entitled CONTROLLING PLUNGER DRIVES FOR FLUID INJECTIONS IN ANIMALS, now abandoned.

CROSS REFERENCE TO RELATED APPLICATIONS

This application is related to previously-filed U.S. patent application Ser. No. 07/881,782 now U.S. Pat. No. 5,279,569 of Charles S. Neer et al., filed May 11, 1992 for METHOD AND APPARATUS FOR INJECTING FLUID INTO ANIMALS AND DISPOSABLE FRONT LOADABLE SYRINGE THEREFOR, which is assigned to the same entity as this application.

REFERENCE TO MICROFICHE APPENDIX

A microfiche appendix is attached to this application. The software in this appendix is subject to copyright protection. The copyright owner has no objection to reproduction of the appendix in the form that it appears in the U.S. Patent and Trademark Office, but reserves all other rights under copyright law.

BACKGROUND OF THE INVENTION

Injectors are devices that expel fluid, such as radiopaque media (contrast fluid) used to enhance x-ray or magnetic images, from a syringe, through a tube, and into an animal subject. Injectors are typically provided with an injector unit, adjustably fixed to a stand or support, having a plunger drive that couples to the plunger of the syringe and may move the plunger forward to expel fluid into the tube, or move the plunger rearward to draw fluid into the syringe to fill it.

Injectors often include control circuits for controlling the plunger drive so as to control the rate of injection and amount of fluid injected into the subject. Typically, the control circuit includes one or more manual switches which allow a user to manually actuate the plunger drive to move the plunger into or out of the syringe; typically the user holds down a "forward" or "reverse" drive switch to move the plunger in the indicated direction.

To reduce the risk of infection, in a typical injection procedure the syringe is only used once, and is disposed after use. In some cases, the syringe is inserted into the injector empty. The empty syringe is filled by retraction of the plunger while the interior of the syringe communicates with a supply of the contrast fluid via an injection tube connected between the nozzle of the syringe and the supply of media. Then, bubbles are removed from the syringe, and the injection is performed. At the end of the procedure, the syringe plunger typically is forward, as is the plunger drive.

In some injectors, the syringe can only be removed or replaced while the plunger drive is fully retracted. As illustrated in FIG. 1A, typically an empty syringe 10 is filled with sterile air, with the plunger 12 at the fully retracted position as shown. The plunger drive includes a jaw 18 designed to engage and disengage a button 14 on the rear side of the plunger while the plunger is in this fully-retracted position. Before an empty new syringe can be filled, it is necessary that the plunger be moved fully forward in the syringe so that the syringe can be filled by rearward retraction of the plunger. Thus, the reloading operation can involve fully retracting the plunger drive to allow removal and replacement of the syringe, then fully advancing the plunger drive and plunger to expel air from the syringe, and then retracting the plunger drive and plunger to fill the syringe. These lengthy, manual movements of the plunger and drive are time consuming.

The above-referenced patent application describes a front-loading injector in which a syringe can be replaced even though the plunger drive is not fully retracted. This injector substantially reduces the number of plunger drive movements necessary to prepare a syringe for a new injection; after an injection, the syringe can be removed and replaced without moving the drive from its fully-advanced position. (The plunger drive jaw 18 can engage and disengage button 14 regardless of the position of the plunger.) After the syringe is replaced, the drive is retracted, filling the syringe for a new injection. Thus, to ready the injector for a new injection, the plunger drive is manually moved once rather than three times.

Another recent development is the use of pre-filled disposable syringes. A pre-filled syringe also reduces the number of manual plunger drive movements necessary to prepare the injector for a new injection. After an injection, the plunger drive is fully retracted, the used syringe is removed and replaced with the pre-filled syringe, and the injector is ready for a new injection. Thus, again, the plunger drive is manually moved once rather than three times.

To prevent infection, contrast media remaining in a syringe after an injection must be discarded. However, contrast media is relatively expensive. For this reason, when preparing for an injection, an empty syringe is filled with only as much media as will be needed for the next injection. For the same reason, pre-filled syringes are sold in a number of capacities, e.g. ranging from 60 to 125 milliliters, allowing the operator preparing for an injection to select a syringe containing only as much media as is needed for the injection.

A typical pre-filled syringe is illustrated in FIG. 1B. In many respects, the pre-filled syringe is identical to the empty syringe shown in FIG. 1A. The barrels 10 and plungers 12 have the same size and profile in both syringes (injectors now in use accommodate only a few FDA approved syringe sizes, e.g., a 200 milliliter size and a 125 milliliter size, so all syringes use these sizes). Furthermore, both syringes have a button 14 which is initially located at the end of the barrel 10 (thus, both syringes are compatible with injectors which are designed to grip a button at the end of the syringe). The main difference is that in the pre-filled syringe of FIG. 1B, the initial location of the plunger 12 is in the middle of the syringe (thus reducing the initial volume of the pre-filled syringe). An extender 16 is attached to button 14 of the plunger, and provides a second button 18 at the end of the syringe which can be gripped by the injector.

SUMMARY OF THE INVENTION

As noted above, at the present state of the art, preparing an injector for an injection requires at least one manual movement of the plunger drive into or out of the syringe barrel, and as many as three such movements. This operation is tedious and inefficient, not only because of the time consumed, but also because the operator must press and hold manual movement switches to produce the movement, and thus is physically tied to the injector and cannot use this time to make other preparations.

In accordance with one embodiment of the present invention, the plunger drive controller has a locked mode in which motion, initially requested by pressing a manual movement switch, will continue whether or not the operator continues pressing the switch, until the plunger drive reaches its fully-advanced or fully-retracted position. Thus, once the controller has entered the locked mode, the operator may release the manual switch and the desired movement, either advancement or retraction, will continue while the operator makes other preparations for the next injection.

In preferred embodiments, the operator causes the controller to enter the locked mode by pressing the manual movement switch for a predetermined period of time. For safety, the manual movement switch may comprise two buttons which must be simultaneously pressed to produce movement. Movement is initiated by pressing both buttons. While both buttons are held down, the plunger drive controller increases the velocity of movement until the velocity reaches a maximum, at which time the plunger drive controller enters the locked mode. If one button is released before the controller reaches maximum velocity and enters the locked mode, the movement will continue, but at a constant velocity. If the second button is released, the movement will stop. Alternatively, if the controller has reached maximum velocity and entered the locked mode, movement will continue even if both buttons are released; however, if thereafter either button is pressed, movement stops. The controller can provide visual feedback, for example via a light which blinks during motion and lights steadily when the controller is in the locked mode. This light may itself move in synchronism with the plunger drive to provide further feedback on the speed of motion.

As noted, the plunger drive controller is typically manually controlled by means of a switch which, when depressed, causes the plunger drive to move in one of two directions. In accordance with a second aspect of the invention, manual control is improved by providing an adjustment allows the operator to adjust the rate at which the plunger drive moves or accelerates. This permits the operator to customize the operation of the plunger drive controller to enhance individual comfort.

In preferred embodiments, the manual control comprises a wheel which, when rotated, causes the plunger drive to move at a speed which is proportional to the speed of rotation. Alternatively, the manual control may be a forward switch and a reverse switch which cause the plunger drive to move in the indicated direction at a programmable velocity or acceleration.

To operate effectively, the plunger drive controller must determine the location of the plunger 12 relative to the ends of the syringe 10 so that, for example, the controller can determine the amount of contrast media remaining in the syringe. This can be done by a sensor which detects the location of the plunger drive jaw 20, which is coupled directly to and moves with the plunger 12. However, a pre-filled syringe may include an extender 16 which changes the relative location of the plunger 12 and the plunger drive jaw 20, leading to malfunction in the plunger drive controller. In accordance with a third aspect of the invention, malfunction is avoided by storing an offset value representative of the length of the extender 16, and applying this offset value to the computed drive jaw position.

In preferred embodiments, the offset value may be computed by querying the operator as to the capacity of the syringe and determining therefrom the appropriate offset value. The controller may be configurable so that this query is not made (for example, if the injector will not be used with pre-filled syringes, and therefore the offset value will not change). Alternatively, the offset value may be automatically computed by detecting physical indicia on the syringe or extender which indicate the length of the extender.

These and other aspects will be further illustrated in the following detailed description with reference to the attached drawings, in which:

DESCRIPTION OF THE PREFERRED EMBODIMENTS

Figure 2A:
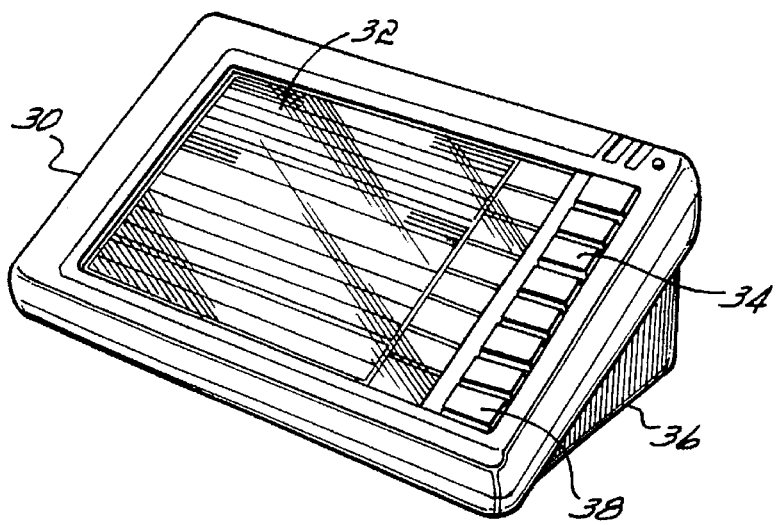
FIGS. 2A, 2B and 2C respectively illustrate the console, powerhead, and powerpack of an injector.
Figure 2B:
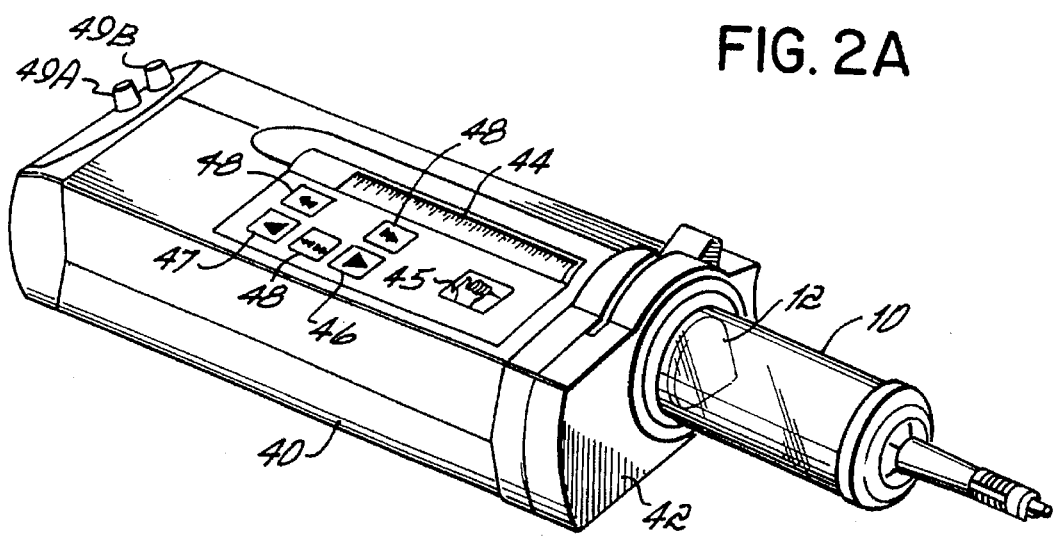
Figure 2C:
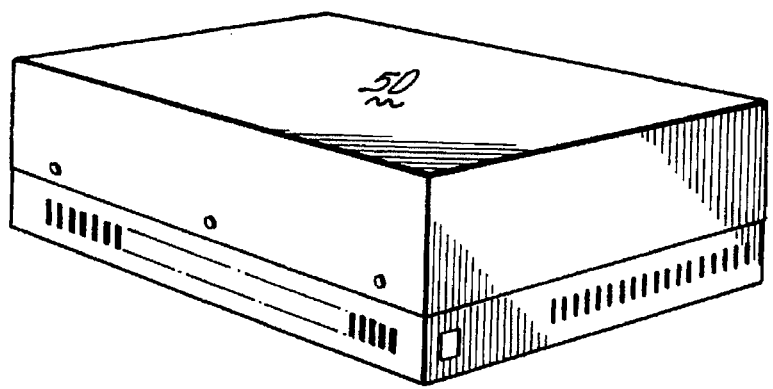

Referring to FIGS. 2A, 2B and 2C, an injection system according to the invention includes three main components, a console 30, a powerhead 40 and a powerpack 50.

The console 30 comprises a liquid crystal display 32 of the type used in notebook computers (e.g., a display sold by Sharp Electronics Corp. of 5700 N.W. Pacific Rim Blvd., Camas, Wash. 98607 as part number LM64P62), coupled to an eight key keypad 34 within a housing 36. As is further elaborated below, display screens presented on display 32 provide injection information and present the user with menus of one or more possible operations, each operation associated with one of the keys on keypad 34.

The powerhead 40 includes a mount 42 (such as that described in the above-referenced patent application) which accepts a syringe 10 for an injection. The powerhead includes a plunger drive motor (not shown) for moving plunger 12 forward into and rearward out of syringe 10 during an injection in accordance with a preprogrammed sequence, or protocol, selected by the operator by operation of the console 30.

The location and movement of the plunger drive is indicated by a light emitting diode (LED) which is mounted to the plunger drive and is visible to the operator through a graduated window 44 in the side of the powerhead 40. As noted below, this LED flashes when the plunger drive is moving, and lights steadily when the plunger drive has been manually locked into forward or reverse motion in the manner described below.

The side of the powerhead 40 includes six pushbuttons: a start/stop button 45, a forward manual motion button 46, a reverse manual motion button 47, and an enable/accelerate button 48. The three enable/accelerate buttons 48 perform the same function; there are three buttons instead of one to improve operator accessibility.

The start/stop button 45 is used to start an injection protocol selected at the console, or to stop and restart an injection. During an injection, all of the eight buttons on the keypad 34 of the console 30 will perform an identical start and stop function. Furthermore, a remote handswitch (not shown) may be connected to the powerpack 50 (see below) to perform a start and stop function. (For this reason, the start/stop button 45 includes a picture of a handswitch.)

To manually move the plunger drive, the operator must simultaneously press a motion button 46 or 47 and an enable button 48. This is a safety feature which reduces the risk of accidental movement of the plunger. If the operator presses the forward button 46 and any of the three enable buttons 48, the plunger will begin forward motion; conversely, if the operator presses the reverse button 47 and any of the three enable buttons 48, the plunger will begin reverse motion. Once motion is initiated in either direction, the operator may release one of the buttons; motion will be maintained at a constant velocity in the same direction so long as any one of the five buttons 46, 47 or 48 is held down. If, instead, after initiating motion in one direction, the operator continues to hold down an enable button 48 and a motion button 46 or 47, motion will not only be maintained in the same direction, but will be accelerated in this direction until either the operator releases one of the buttons or a maximum velocity is achieved. At any time during the acceleration, the operator may release one of the buttons and hold down the other, and the motion will continue at the same velocity without acceleration. Thereafter, the operator can re-depress the released button, at which time acceleration will begin again.

If the velocity of motion increases to a maximum value, the plunger drive controller (described in more detail below) will enter a locked mode. In this locked mode, movement will continue at the maximum velocity in the same direction even if the operator releases all of the buttons. This frees the operator to perform other tasks when preparing for an injection without being forced to hold manual buttons on the injector until the plunger drive has made the lengthy transition to its fully-advanced or fully-retracted position.

For safety reasons, the locked mode can be terminated readily. If the operator has entered the locked mode and thereafter released all of the buttons, if at any time thereafter any of the buttons is pressed, the plunger drive controller will exit the locked mode and terminate motion.

Two lights 49A and 49B mounted on the rear of the powerhead 40 indicate the status of operation of the injector. Light 49A is an injecting/fault indicator. This light glows while an injection is in process. It will flash if an error is detected. Light 49B is an enabled indicator. It glows when the injector has been enabled and is ready to perform an injection protocol.

The rear end of the powerhead 40 (opposite mount 42) includes a jog wheel or switch (not shown in FIG. 2B, see 163, FIG. 5) used, in the manner described below, to manually activate motion of the plunger drive.

The powerpack 50 illustrated in FIG. 2C contains electronics which communicate with the console 30 and powerhead 40 to perform the functions described above. The powerpack is connected to the console 30 and powerhead 40 by standard computer communications cables (not shown). Signals carried on these cables are interfaced to circuitry inside of the powerhead, console, and powerpack in a manner described below.

Figure 3:
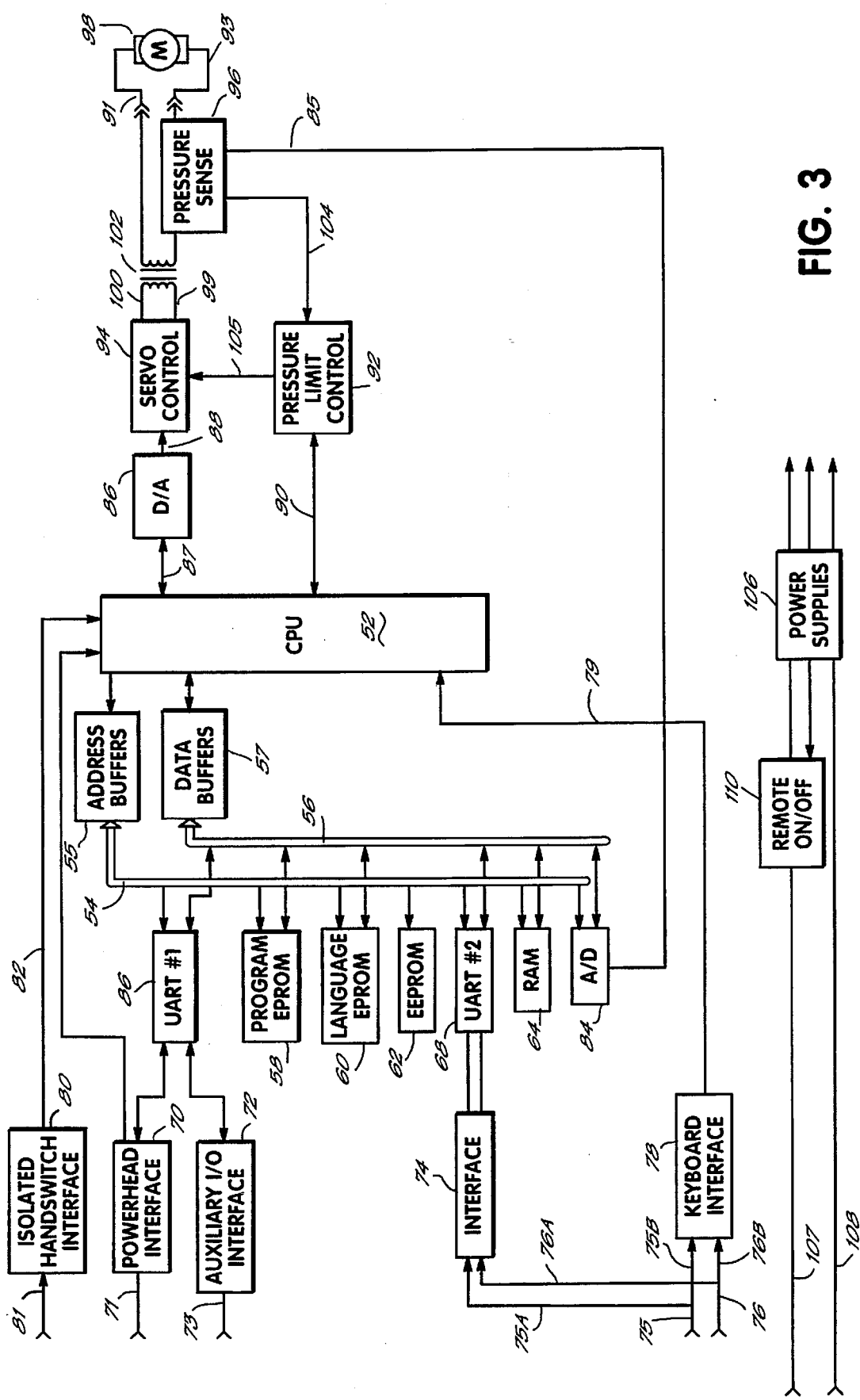
FIGS. 3, 4, and 5 are electrical and electrical-mechanical block diagrams of the powerpack, console and powerhead, respectively.

As shown in FIG. 3, the circuitry in the powerpack includes a central processing unit (CPU) 52 which controls the operations of the powerhead 40 and console 30. The CPU is preferably a programmable microprocessor such as the MC68332FN microprocessor, manufactured by Motorola, 2110 East Elliot, Tempe, Ariz. 85284. This microprocessor is a member of the 68000 family of microprocessors and features multitasking support; it is designed for use in so called "embedded" environments such as the circuit described herein, and therefore has more than the usual number direct-wired input-output ports.

The CPU connects to an address bus 54 for addressing a number of memory and communications components and a data bus 56 for retrieving and/or sending data from and to these components. Buffers 55 and 57 aid CPU 52 in interfacing to the address and data busses, respectively. Each of the elements connected to the address and data busses are briefly described below.

An erasable programmable read-only memory (EPROM) 58 connected to data bus 56 contains the program software which operates the CPU 52. The EPROM contains an operating system, which performs low-level management of the CPU and its communications with other circuits, and a custom program for controlling the console and powerhead to perform injection protocols. In one embodiment, the operating system software is the USX68K operating system, a multi-tasking operating system for 68000 series microprocessors sold by U.S. Software of 14215 N.W. Science Park Drive, Portland, Oreg., 97229, and the custom program is written in the "C" programming language. This custom program is described below, and a copy of the "C" language source code for the custom program appears in the appendix to this application.

A second EPROM 60 connected to data bus 56 contains language information used by the program software in EPROM 56 when generating displays for presentation on the display 32 (FIG. 2A). As will be further elaborated below, the display screens presented on the display 32 include textual descriptions of actions being taken by the injector, and menu selections which the operator can select. The textual portions of these display elements are stored in the language EPROM 56, from which they are retrieved and inserted into a template as CPU 52 is producing a display screen. Preferably, the language EPROM contains multiple versions of each textual insert, representing different languages, so that the operator can, through menu choices entered at the console keypad 34, choose a preferred language in which to generate screen displays. An exemplary set of languages suitable for the North American and European markets would be English, German, French and Spanish.

Figure 1A:
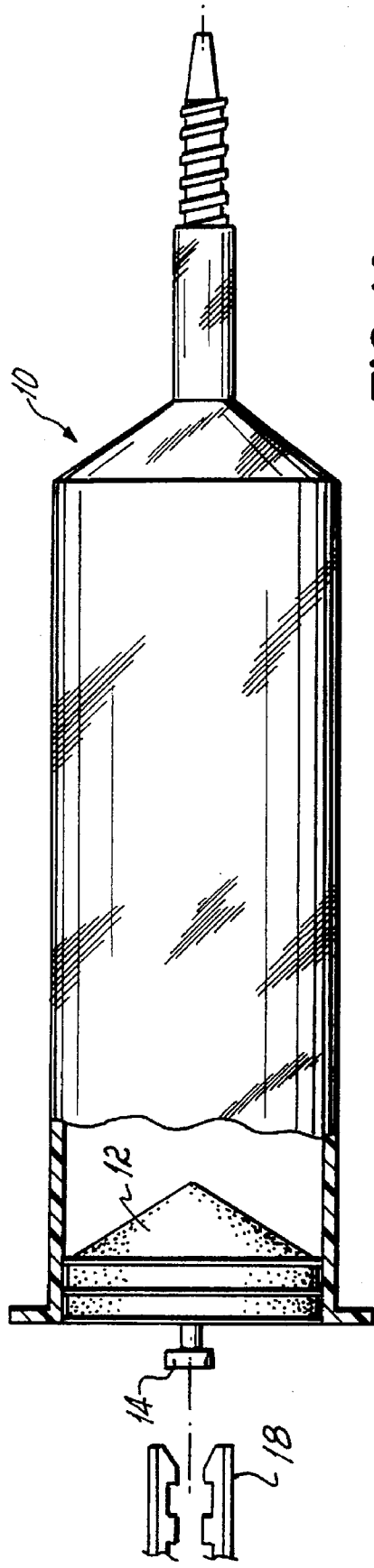
FIGS. 1A and 1B are side, partial cut-away views of an empty syringe and a pre-filled syringe, respectively.
Figure 1B:
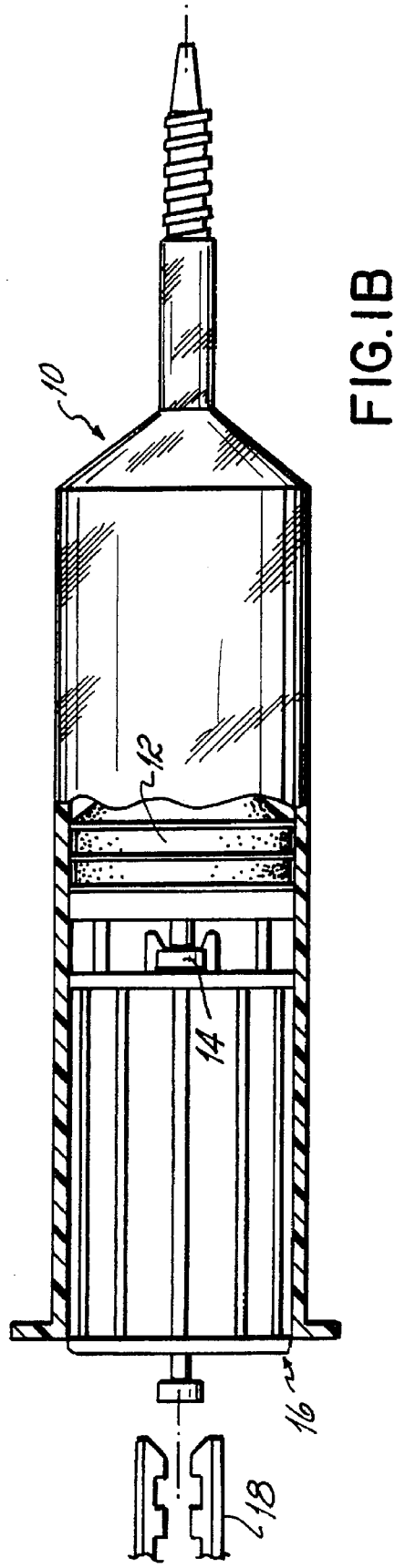

A third, electrically erasable and programmable read only memory (EEPROM) 62 is attached to the data bus. EEPROM 62 stores data in a non-volatile manner (so that it will not be lost when the power is turned off). Among other things, EEPROM 62 stores preprogrammed injection protocols. These protocols are created and stored by the user as desired (details are reviewed with reference to FIG. 6A, below). In addition, EEPROM 62 stores calibration information, used by CPU 52 in interpreting fluid pressure and plunger position information which it receives while performing an injection. Further, EEPROM 62 stores information on the most recently completed injection, such as the injection time and volume, so that this information may be retrieved by the operator. EEPROM 62 also stores operator preference data entered by the operator into the console (see FIG. 6E, below). This includes the preferred display language, time, and date formats. Moreover, EEPROM 62 stores operating parameters such as a programmable pressure limit, and a flag (used in the manner described below) indicating whether the injector will be used with partially pre-filled syringes of the kind illustrated in FIG. 1B. Finally, EEPROM 62 stores the registered name and/or number of the machine owner, to facilitate service and on-line customer support.

Data bus 56 is also connected to a random access memory (RAM) 64 which is used by the operating system to store a stack of register values generated during CPU operations and machine state information corresponding to currently inactive processes running on the CPU. The application software uses the remaining Space in RAM 64 (as managed and allocated by the operating system) to store variables computed and manipulated during operation of the injector.

Most communications between CPU 52 and the powerhead 40 and console 30 flow through one of two universal asynchronous receiver/transmitters (UARTs) 66, 68 which are connected to the data bus. A UART is a communications circuit, generally available in integrated circuit form, which collects and buffers incoming and outgoing information to enable asynchronous communications between processors or computing systems over a data link. A suitable UART is the MC68681, sold by Motorola. The first UART 66 is responsible for communications with the powerhead circuitry (see FIG. 5, below), which pass through an interface 70 and a communications cable 71 connected to the powerhead. (However, pulses from the optical encoder 166 on the powerhead (FIG. 5, below) travel directly from interface 70 along line 71 to an interrupt input on the CPU 52.) UART 66 also handles communications with an auxiliary interface 72, which can be coupled through a communications cable 73 to a printer to allow CPU 52 to print records of an injection. Alternatively, interface 72 (or another, similar interface) can be used to attach CPU 52 to a remote computer or other external device to allow remote monitoring and/or control of the injector.

The second UART 68 is responsible for communication with the console 30 (FIG. 2A). Two consoles 30 can be connected to the powerpack via cables 75, 76.

Cables 75 and 76 carry data representing keystrokes and screen activity between the powerpack 50 and console 30. This data is encoded in a communications protocol and transmitted in accordance with the RS422 standard. The encoded data is carried via lines 75 and 76 to interface 74 which encodes and decodes transmissions for a second UART 68. UART 68 routes keystrokes received by either console via interface 74 to CPU 52 via the data bus 56, and further routes display information produced by CPU 52 to interface 74 for transmission to the consoles via lines 75A and 76A.

Cables 75 and 76 also include, on separate conductors, lines 75B and 76B, which carry logical signals corresponding to key 38 (FIG. 2A) of each console keyboard. As elaborated below, the software driving the console displays is written so that key 38 is the most frequently used key—depending on the screen being displayed, key 38 will function as an "Exit" key to depart the screen, an "Enter" key to accept a value or selection and depart the screen, or a "Disable" or "Cancel" key to terminate an operation. (Exemplary screens are discussed below with reference to FIGS. 6A–6F.) Because key 38 is the most frequently used key, and because key 38 is used for time-sensitive input such as a cancel command, key 38 is connected to the CPU 52 differently than the other keys. Key 38 is connected directly to the CPU 52 via an interrupt line 79; when a keystroke is detected, a non-maskable interrupt interface (NMI) 78 (which essentially constitutes a RS422 transmitter and receiver which converts the signal on lines 75B and 76B to a clean logic signal on line 79) sets an interrupt on line 79, which is immediately detected and subsequently serviced by CPU 52.

A similar interface is used for the remote handswitch. The cable 81 leading from the handswitch connects to the handswitch interface circuit 80 which among other things, electrically isolates the handswitch from the powerpack ground, and "de-bounces" the handswitch (eliminates electrical noise created when the switch is pressed or released) so as to provide a clean logic signal indicating whether the handswitch button is being pressed or is released. This logic signal is connected, via line 82, to a time processor unit (TPU) port on CPU 52. CPU 52 reads the logic signal at this TPU port and responds appropriately according to the software in EPROM 58.

The last component on the CPU data bus 56 is an analog to digital converter (A/D) 84. This converter is used to generate a digital signal, readable through data bus 56, which corresponds to an analog signal received on line 85. A suitable A/D converter is the LT1094, sold by Linear Technology of 1630 McCarthy Blvd., Milpitas, Calif. 95035. A/D converter 84 is used by the motor servo control circuitry described below. The CPU has two additional interfaces to the motor servo control circuitry: an interface on line 87 to a digital to analog converter (D/A) 86 (which generates an analog signal on line 88 corresponding to a digital signal received on line 87, for example the AD7245, sold by Analog Devices of One Technology Way, P.O. Box 9106, Norwood, Mass. 02062), and a second interface on line 90 to pressure limit control circuit 92. These interfaces (lines 87 and 90) connect to synchronous peripheral interface (SPI) channels on the microprocessor, and are controlled in accordance with the software in EPROM 58.

The D/A 86, A/D 84, servo control 94, pressure limit control 92, and pressure sense 96 circuits collectively form a motor servo control circuit which controls the operation of the motor 98 which drives the syringe plunger into and out of the syringe. (Motor 98 is shown for clarity, but it should be understood that motor 98 is physically located in the powerhead 40 (FIG. 2B, 5); lines 91 and 93 connect to the motor through several conductors of the computer interface cable connecting the powerhead 40 and the powerpack.)

Servo control circuit 94 responds to an analog voltage produced by D/A 86 on line 88 and produces a corresponding voltage between lines 99 and 100. The voltage on lines 99 and 100 is transformed by transformer 102 to a level sufficient to drive motor 98 via lines 91 and 93. Servo control circuit 94 contains a flyback transformer circuit which produces an output voltage related to the duty cycle of a switching FET. This duty cycle is produced by a UC3525 pulse width modulation (PWM) circuit—an integrated circuit which produces a 100 kHz digital output signal having a duty cycle which varies from 0% to 50% in response to an analog input voltage on line 88. A suitable PWM circuit is the UC3525, sold by Unitrode of 7 Continental Boulevard, Merrimack, N.H. 03054. Thus, CPU 52 controls the speed and power output of motor 98 by writing a digital word representing a desired output voltage to D/A 86 via lines 87; this digital word is then converted to an analog signal, and the analog signal is converted to a pulse width modulated control signal in the servo control, resulting in the desired output voltage at the motor.

Pressure sense circuit 96 includes a current sense circuit of which detects the current flow through line 93 (i.e., through the motor) and produces analog signals on lines 104 and 85 proportional to the detected current. In essence, this current sense circuit comprises a low-value, high power rating resistor in series with line 93 which attached to the motor 98. A differential voltage amplifier (based on a low-noise, high common mode rejection op-amp) senses the voltage across the resistor and converts it to an analog voltage on lines 85 and 104. The current flow through the motor is proportional to the force exerted by the motor and therefore to the injection pressure. Thus, the analog signals produced by pressure sense circuit 96 can be used to derive the injection pressure.

Pressure limit control circuit 92 uses the analog signal on line 104 to perform a hardware pressure control function. Pressure limit control circuit 92 contains a commercially available digital potentiometer, used to produce an analog comparison voltage. A suitable potentiometer is the DS1267, sold by Dallas Semiconductor of 4350 Beltwood Parkway South, Dallas, Tex. 75244. CPU 52 (via lines 90) programs this potentiometer to produce a comparison voltage corresponding to the maximum allowable pressure. Pressure limit control circuit 92 includes a comparator which compares the analog signal on line 104 produced by pressure sense circuit 96 to the comparison voltage. If the pressure exceeds the maximum allowable pressure (indicating a failure in the CPU 52), a digital signal is transmitted on line 105 to servo control circuit 94, which in response ignores the analog signal on line 88, and instead reduces the voltage on lines 99 and 100 to halt the motor. Thus, once the CPU 52 has programmed pressure limit control circuit 92 with the correct maximum pressure, the injector will not exceed this pressure even if the CPU 52 fails.

Under normal conditions, this hardware pressure limit will not be activated, because CPU 52 continuously obtains feedback on the performance of the motor and the pressure produced and controls the motor through D/A 86 to achieve the desired injection protocol. CPU 52 obtains feedback on an ongoing injection from three sources: (1) feedback on the injection pressure is obtained from A/D 84, which produces a digital word on bus 56 corresponding to the analog voltage on line 85 produced by pressure sense circuit 96; (2) feedback on the motor speed is obtained from an optical encoder 166 physically coupled to the motor inside of the powerhead 40 (elaborated with reference to FIG. 5, below); and (3) feedback on the position of the plunger inside of the syringe is obtained from a linear potentiometer 168 physically coupled to the plunger (see FIG. 5, below). Using this information, CPU 52 carefully controls the injection pressure, volume and speed according to a pre-programmed protocol under control of software in EPROM 58.

Power for the powerpack, powerhead, and console display is supplied by the AC power lines 107 and 108. The AC line voltage is conditioned by a conventional power supply circuit 106 which includes a transformer which can be adjusted for use with non-United States line voltages, and a voltage sense circuit for selecting the appropriate transformer based on the detected line voltage. The power may be turned off by unplugging the injector, or preferably by a toggle switch which opens and closes a solid-state relay in remote on/off circuit 110.

Figure 4:
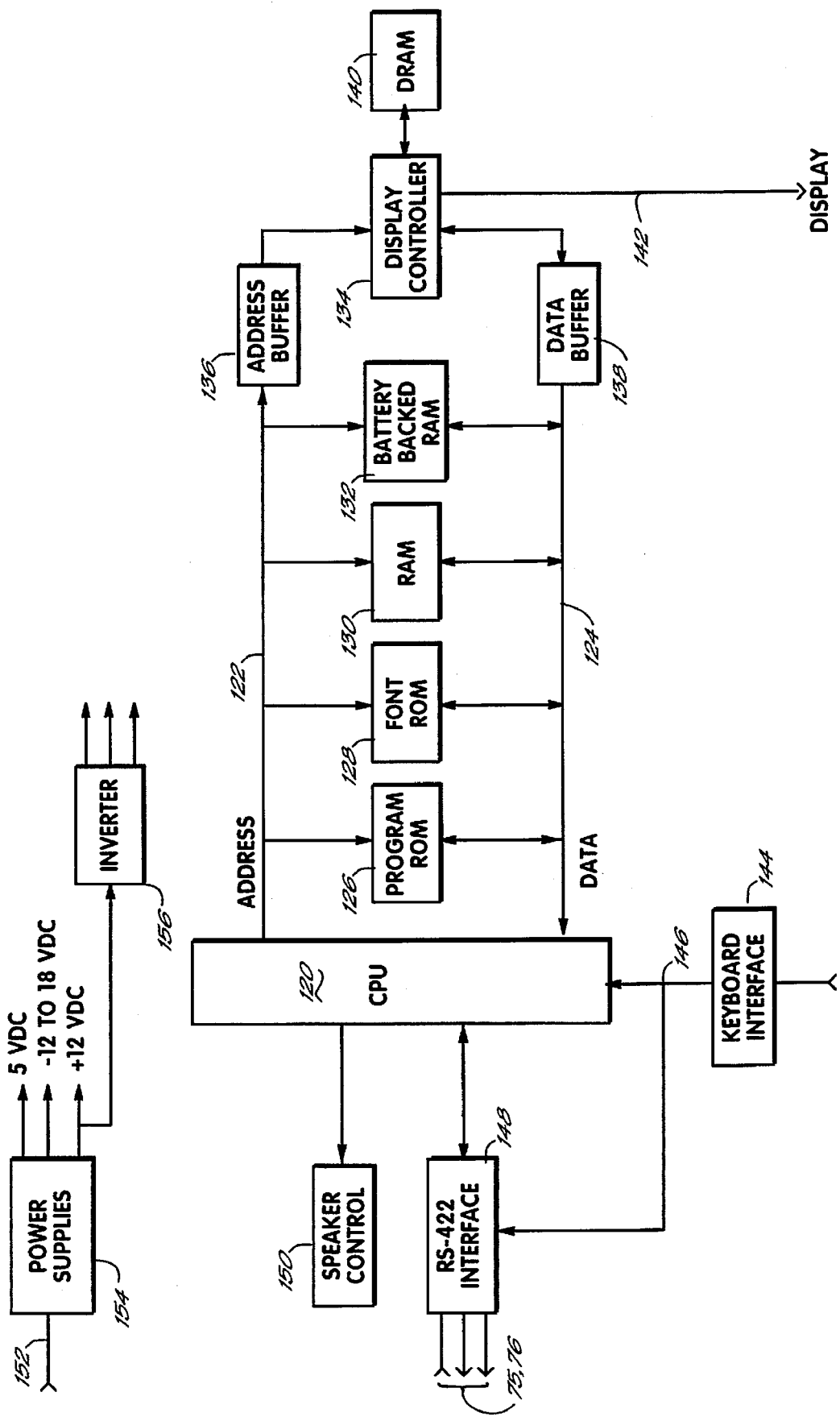

Referring to FIG. 4, the console circuitry is also built around a general purpose CPU 120. A suitable microprocessor is the MC68332FN. The address bus 122 and data bus 124 connected to CPU 120 connect to a number of supporting circuits. Program ROM 126 contains the software which directs CPU 120. (This software is written in assembly language, and is included in the attached appendix). Font ROM 128 includes font information retrieved by CPU 120 in producing fonts for text generated on the display screen. These fonts include foreign-language characters where necessary to support foreign language text. RAM 130 is used by microprocessor in performing display and retrieval operations. Battery-backed RAM 132 stores the current time of day, so that the powerpack may make a date and time-stamped record of an injection.

The primary function of the console circuitry is to generate screens on the display 32, and to receive keystrokes from the eight-key keypad 34 (FIG. 2A) and relay the keystrokes to the powerpack. Displays are generated by a display controller 134, such as the F82C455 VGA controller sold by Chips & Technologies of 3050 Zanker Road, San Jose, Calif. 95134. This VGA controller interacts with CPU 120 via an address buffer 136 and data buffer 138, and stores screen information in a dynamic random access memory (DRAM) 140. Information is sent over lines 142 to the display 32.

Keystrokes from the keypad are received by keyboard interface circuit 144 which "debounces" the keystrokes, producing clean logic signals on lines 146. These logic signals are fed back to CPU 120 so that it may confirm keystrokes by producing an audible tone through speaker control circuit 150. Speaker control circuit also generates unique audible signals to indicate other operations, such as the initiation of an injection, or to notify the operator that scanning should begin. A suitable controller is the MC3487, sold by Motorola.

CPU 120 communicates with the powerpack via an RS422 interface circuit 148 which sends and receives digital signals over lines 75 and 76. Interface circuit 148 also receives and forwards keystrokes directly from keyboard interface 144. The eight keys on the console form a single, eight bit byte of information (where each bit indicates whether the key is pressed or released). This byte is coupled directly to CPU 120 via a "245" type logical buffer.

+28 Volt DC power is received from the power supplies in the powerpack via lines 152. A power supply circuit 154 regulates this +28 Volt DC power line into a collection of supply voltages, as needed by the various circuitry in the console. Furthermore, a power inverter circuit converts +12 Volt DC power produced by the power supply circuit 154 into low-current 600 Volt AC power supplies for energizing the liquid crystal display.

Figure 5:
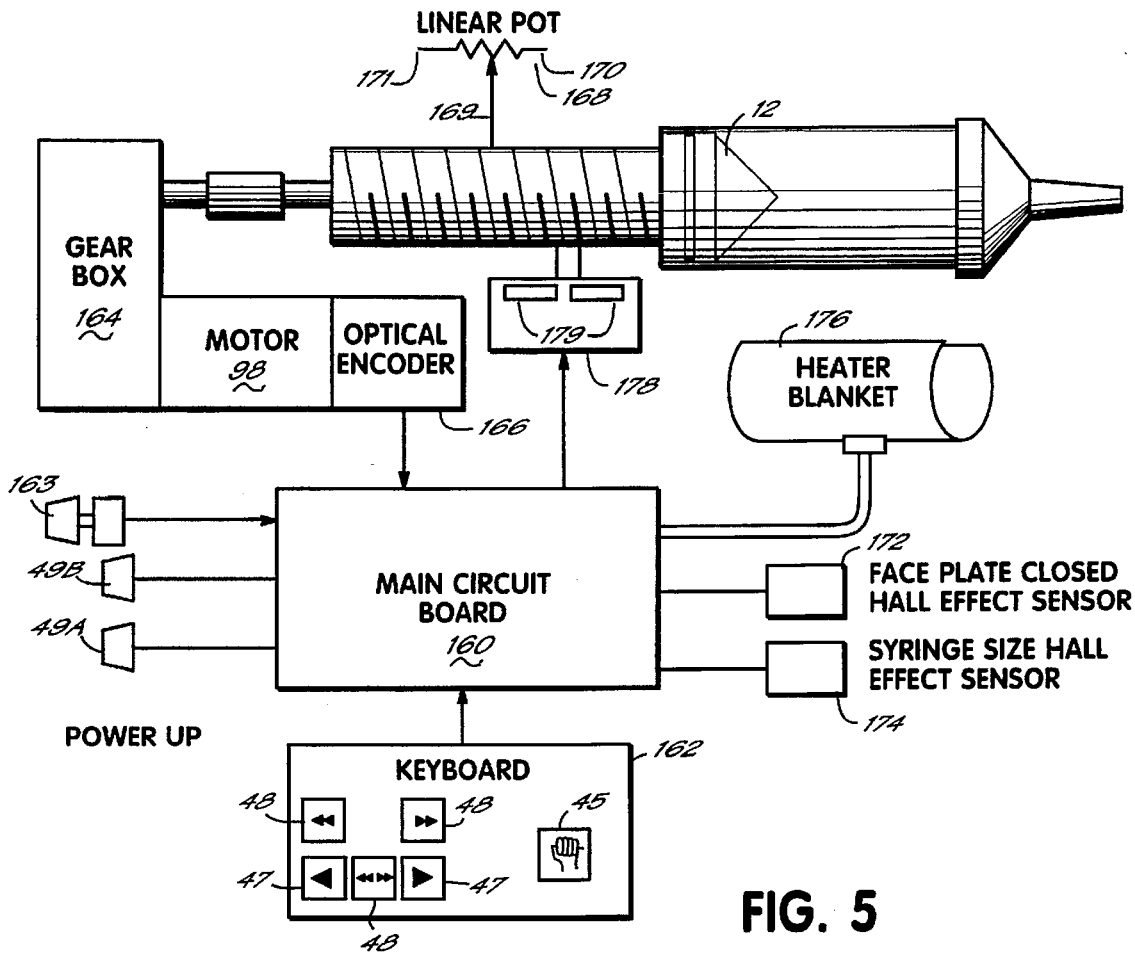

Referring to FIG. 5, the powerhead also includes a circuit board 160 including microprocessor to perform communications with the powerpack 50 (FIG. 2C). A suitable microprocessor is the 68HC11E2, sold by Motorola, which is a low-cost, minimal functionality microprocessor in the 68000 family. The circuit board receives and forwards keystrokes from the buttons on the keyboard 162 (described above), and electrical pulses indicating movements from the manual knob 163 mounted on the rear of the powerhead. A suitable manual knob is the model 600 thumbwheel, sold by Clarostat of 1 Washington Street, Dover, N.H. 03820. The circuit board also lights and extinguishes the injecting/fault indicator light 49A and the enabled indicator light 49B.

The motor 98 is coupled to a gear box which translates rotary motion of the motor to linear translation of the plunger. One suitable motor is the CYMS A2774-2 motor, sold by Barber-Colman, P.O. Box 7040, Rockford, Ill. 61125. The rotation of the motor is detected by optical encoder 166 (encoder 166 essentially comprises a pinwheel which rotates between a light source and a light detector to produce electrical pulses, for example the HEDS-9100 encoder, sold by Hewlett-Packard of 3003 Scott Boulevard, Santa Clara, Calif. 95054). Encoder 166 sends electrical pulses to circuit board 160, which relays them to powerpack 50, allowing CPU 52 on the powerpack to monitor movement of the motor.

The position of the plunger is detected by a linear potentiometer 168, for example the LCPL200, sold by ETI Systems of 215 Via Del Norte, Oceanside, Calif. 92054. The wiper 169 of potentiometer 168 is mechanically coupled to and moves with the plunger 12. A DC voltage drop is placed across the potentiometer terminals 170 and 171, and as a result, an analog voltage representative of the location of the plunger and wiper 169 is produced at the wiper 169. An A/D converter on circuit board 160 converts this analog voltage to a digital signal which circuit board 160 forwards to the powerpack 50.

Circuit board 160 also detects the output of two Hall effect sensors 172 and 174. The powerhead has a removable face plate 42 (FIG. 2B). There are currently two different face plates having differently-sized apertures for accepting differently-sized syringes. Thus, although the face plate need not be removed to replace the syringe, it may be removed to use a different syringe size. Sensor 172 detects whether face plate 42 is open, and if so circuit board 160 sends a message to powerpack 50 which prevents any further injection procedures until the face plate is closed. Sensor 174 detects the size of the face plate in use. Currently, only one of the two face plates includes a magnet which triggers sensor 174; thus, circuit board can determine which face plate has been installed by determining whether sensor 174 has been triggered. This information is also forwarded to CPU 52 in the powerpack so that CPU 52 may compensate for the different syringe sizes when controlling motor 98 (as described below).

At the direction of CPU 52, circuit board 160 also controls heater blanket 176, which heats the contrast fluid in the syringe. Furthermore, circuit board 160 controls movement indicator board 178. Movement indicator board 178 is mechanically coupled to the plunger 12 and includes two light emitting diodes LEDs 179 which are visible through window 44 on the powerhead (FIG. 2B). LEDs 179 provide the operator with feedback on the position of the plunger, by correlating the position of the diodes with the graduated scale on window 41. The two sides of the window 41 contain different graduated scales: one calibrated for large syringes and one for small syringes. Depending on the syringe size detected by sensor 174, the LED next to the appropriate graduated scale is illuminated. Furthermore, as discussed in more detail below, when the plunger is moving, CPU 52 directs circuit board 160 to flash the LED. Also, when the CPU 52 enters its "locked mode" (discussed above), CPU 52 directs circuit board 160 to steadily light the LED. Thus, LEDs 179 provide operator feedback on the plunger position, direction of motion, and the "locked mode".

Figure 6A:
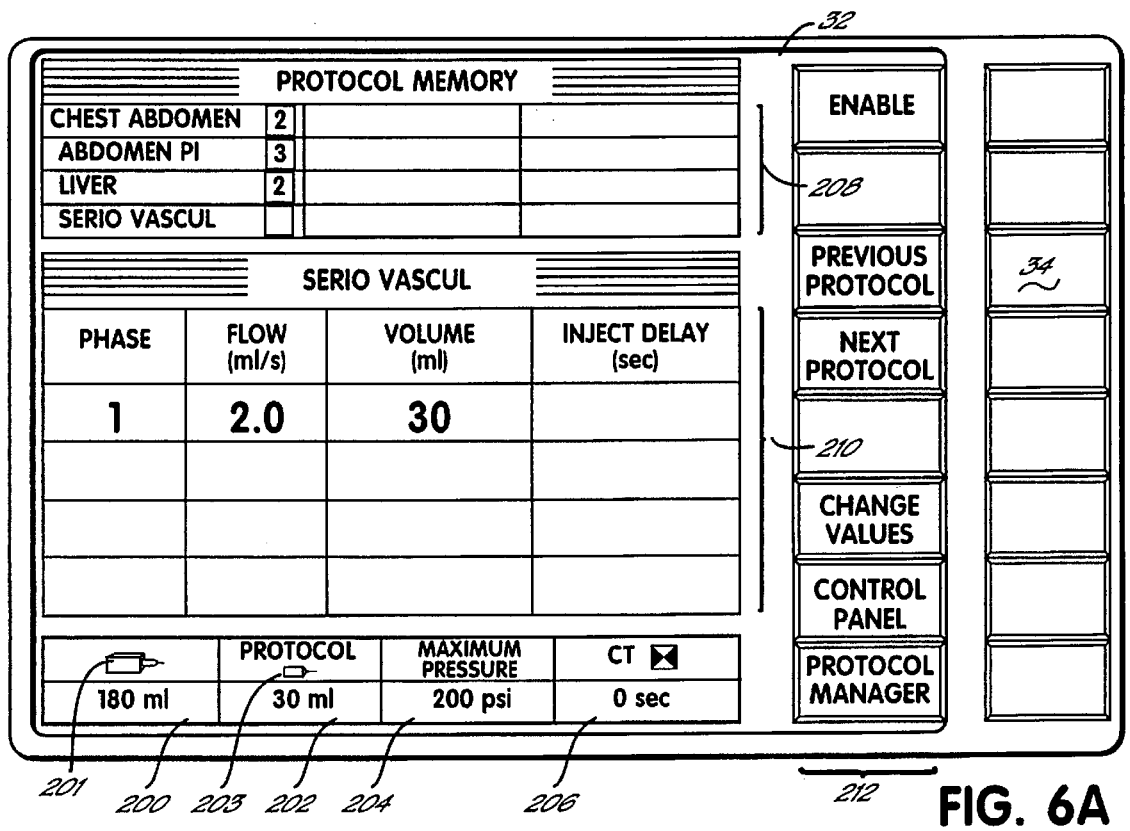
FIGS. 6A, 6B, 6C, 6D, 6E and 6F are illustrations of displays produced by the console in operation of the injector.

Referring to FIGS. 6A–6F, an injection protocol will be described from the operator's perspective. The main operating screen is illustrated in FIG. 6A. Box 200, which is associated with an iconic representation 201 of the powerhead, identifies the current volume of contrast media in the syringe. Box 202, which is associated with an iconic representation 203 of the syringe, identifies the total volume which has been dispensed during the currently selected protocol. Box 204 identifies the pressure limit pre-selected by the operator for the procedure, and box 206 identifies a scan delay (in seconds), which is the delay from the time the operator initiates an injection (either with the handswitch, a key on the console or a button on the powerhead) until the x ray or magnetic scan of the subject should begin (at the end of this delay, CPU 120 produces a tone indicating to the operator that scanning should begin; alternatively, scanning could be automatically initiated by a suitable electrical connection between the scanner and injector). In the illustrated situation, the syringe contains 180 ml of fluid, 30 ml of which will be used by the currently selected protocol, the pressure limit is 200 psi and there is no scan delay.

In the display illustrated in FIG. 6A, the upper regions of the screen display stored injection protocols. Region 208 identifies protocols which the operator may select, and region 210 gives details of the currently selected protocol. As shown in region 210, a protocol comprises a number of phases; during each phase the injector produces a pre-programmed flow rate to output a pre-programmed total fluid volume. The illustrated protocol "SERIO VASCUL" has only one phase; however, other protocols which can be selected by the operator have multiple phases. In region 208, protocols are identified by name and by number of phases; thus, as illustrated, the "LIVER" protocol has 2 phases and the "ABDOMEN PT" protocol has 3 phases.

The user can select protocols, enable an injection, and otherwise navigate through display screens by pressing the buttons on the keypad 34 next to the display. Region 212 of the display is dedicated to identifying the functions available from the buttons on the keypad 34. Thus, in this display illustrated in FIG. 6A, the user may select the previous or next protocol in the list in region 208 by pressing the buttons next to the words "PREVIOUS PROTOCOL" and "NEXT PROTOCOL", respectively, on the display. The user may also change and store the flow, volume and inject delay values for the current protocol by pressing the button next to "CHANGE VALUES"; doing so will alter the function of the keypad and region 212 of the display, so that the operator may select a value, increment and decrement the value, select characters to form or edit a protocol name, and then return to the display shown in FIG. 6A. From FIG. 6A, the operator may also enter a control panel display (see FIG. 6E, below) to adjust operating parameters and other data. Also, the operator may enter a protocol manager in which the operator may rename or delete protocols, and may determine the order of the protocol list shown in region 208. Finally, the user may also enable an injection from the display illustrated in FIG. 6A by pressing the button next to "ENABLE".

Figure 6B:
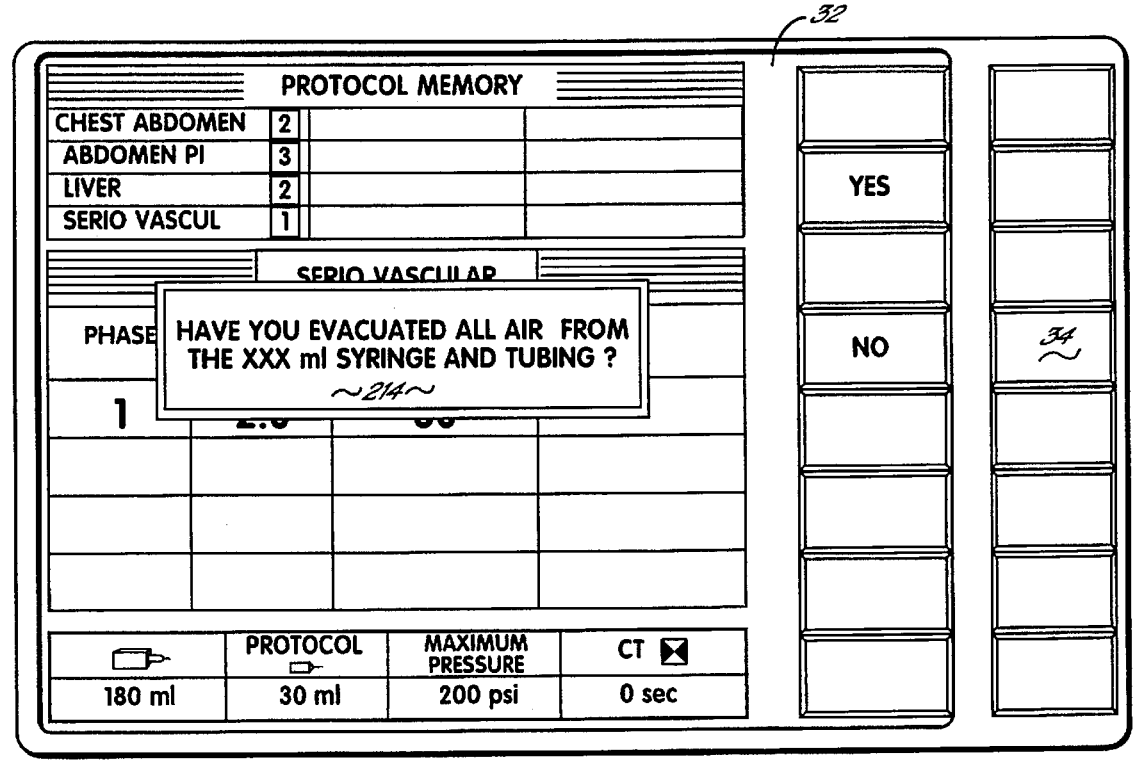

As shown in FIG. 6B, when the user enables an injection, as a safety measure, the injector first presents a text box 214 which asks the operator whether all of the air has been evacuated from the syringe. Region 212 of the display contains only the words "YES" and "NO", indicating that the operator must answer the question as either yes or no. If the button next to "NO" is pressed, the injection will be cancelled. If the answer is "YES", the injector will proceed to an enabled state, illustrated in FIG. 6C. Here, region 208 of the display indicates the expected duration, and region 212 includes the word "START", "AUTO ENABLE" and "EXIT". If the operator presses the button next to "EXIT", the injector will return to the state illustrated by FIG. 6A. If the operator presses the button next to "AUTO ENABLE", the injector will toggle into and out of the auto-enabled mode, as confirmed by a briefly-displayed box in the center of the screen. If the operator presses the button next to "START" the injection will begin and the injector will move to the state illustrated by FIG. 6D.

Figure 6C:
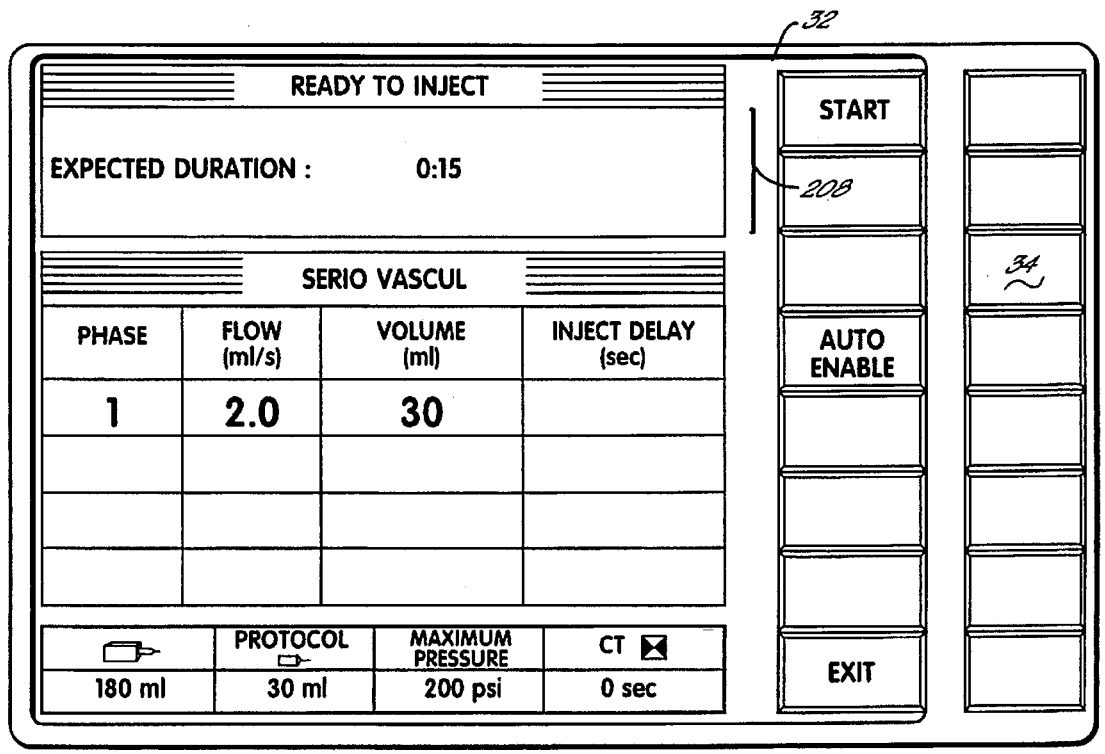
Figure 6D:
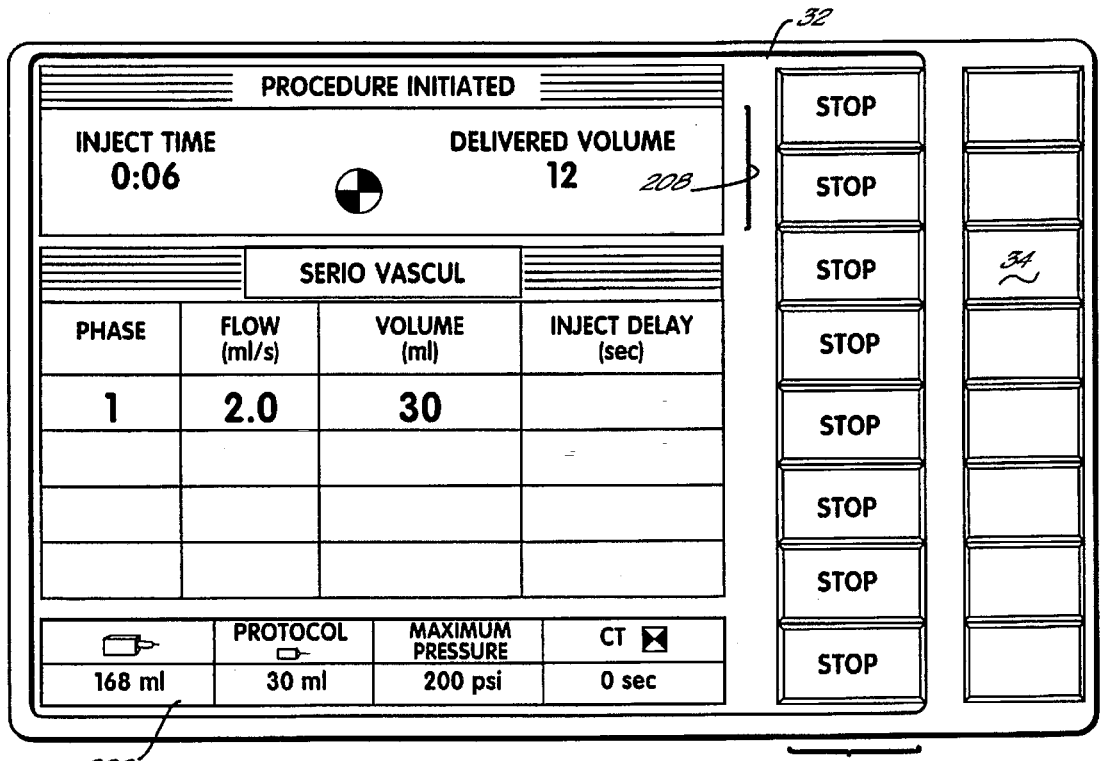

While an injection is proceeding, the display shown in FIG. 6D is displayed. In this display, region 208 indicates the total injection time and the volume (in ml) delivered to the patient. Region 212 shows the word "STOP" next to each of the buttons on the keypad 34, indicating that the operator may stop the injection by pressing any of the buttons (or by pressing the start/stop button 45 on the powerhead, or by pressing the handswitch). In addition, in box 200, the total volume of fluid in the syringe counts down as fluid in injected into the subject.

After the injection protocol has completed, the injector will return either to the state illustrated by FIG. 6A or to the state illustrated by FIG. 6C. If the operator put the injector in the auto-enable mode by pressing "AUTO ENABLE" at FIG. 6C, the injector will return to the state illustrated by FIG. 6C. However, if the operator did not put the injector into the auto-enable mode, the injector will return to the state illustrated by FIG. 6A. Thus, by placing the injector in auto-enable mode, the operator can more easily repeat an injection protocol; this can be useful where, for example, the contrast media dissipates relatively rapidly, and multiple images will be taken on the same area of the subject. By using "AUTO ENABLE", the operator may replenish the contrast media just before each image by pressing a single key (or the handswitch), without re-enabling the injector.

As noted above, injection operators may wish to use prefilled syringes for injections. However, prefilled syringes often include extenders which reduce the filled volume of the syringe (syringes of this type are known as "partial pre-filled" syringes). The injector described herein includes a feature for compensating for the reduced volume of partial pre-filled syringes, described below.

Figures 6E, 6F:

As noted above, to set up the injector, the operator may enter the "Control Panel", illustrated in FIG. 6E. In the control panel, the display identifies the current operational settings of the injector. Thus, the control panel includes a box 220 which identifies the current pressure limit, a box 222 which identifies the current language (as noted above, the operator may choose a language for the textual portions of the display), boxes 226 and 228 which identify the current time and date, and a box 230 which identifies the owners registration name and/or number. This information is entered using the keypad and region 212 of the display in the manner discussed above.

An additional box 232 on the "Control Panel" display is used to indicate whether partial pre-filled syringes will be used with the injector. Box 232 will include the word "YES" or "NO", as selected by the operator (as shown in FIG. 6E, when the user attempts to modify this box, region 212 of the display provides a menu with the choices "YES" or "NO").

If the operator has modified box 232 to indicate that partial pre-filled may be used (i.e., box 232 has a "YES"), then the enable procedure described above is modified slightly. If partial pre-filleds may be used, after the operator enables an injection by pressing "ENABLE" at the display of FIG. 6A, the injector presents the screen illustrated in FIG. 6F, in which the operator must identify the pre-filled syringe size by pressing a button next to "50 ml", "65 ml", "75 ml", "100 ml", or "125 ml". Once the operator has identified the pre-filled syringe size, the injector will continue to the display illustrated in FIG. 6B. CPU 52 (FIG. 3) will then compensate for the extender in the syringe, in the manner described below with reference to FIG. 7B.

Figure 7A:
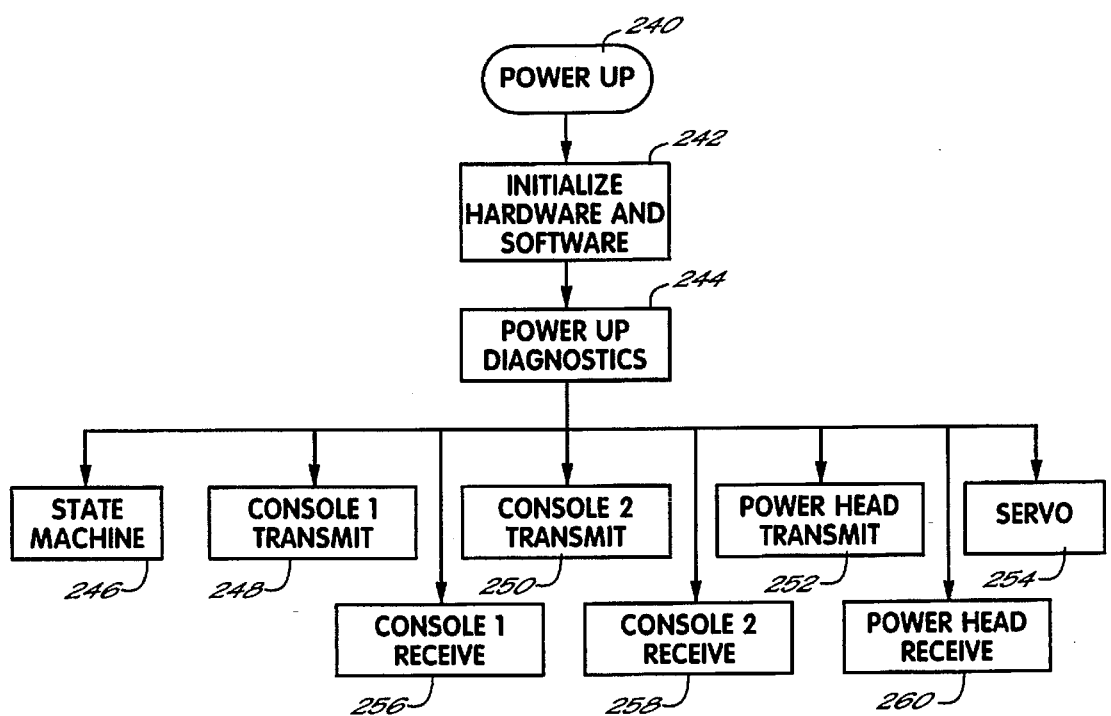
FIGS. 7A, 7B, 7C, 7D, 7E, 7F and 7G are flow charts illustrating the software operating within the power pack.

Referring to FIG. 7A, the program operating in CPU 52 is initiated 240 when the power is turned on. The program first initializes 242 the hardware and software attached in powerpack 50, powerhead 40 and display 30. Then, CPU 52 performs 244 diagnostics to ensure that the injector is operating properly; essentially, this involves sending test data to various hardware elements and verifying that the appropriate responses are received.

After these diagnostics have passed, CPU 52 initiates a number of "threads", or parallel processes; thereafter, these processes are time-multiplexed on CPU 52 under control of the above-described USX68K operating system. These threads communicate with the operating system and with each other by "messages" or semaphores—essentially, inter-process communications are placed in a globally accessible area, managed by the operating system, where they can be later retrieved by other threads. The operating system allocates processing time to the threads. Much of the time, a thread will be "inactive", i.e., it will not have any pending operations to perform. The threads are generally written so that, if the thread is inactive, it will notify the operating system of this fact ("return time" to the operating system) so that the operating system can reallocate processing time to another thread.

The operating system allocates processing time to threads in a prioritized, round-robin fashion. Thus, the operating system will provide processing time to each thread generally in turn; if an active, low-priority thread uses more than a maximum amount of processing time, the operating system will interrupt the thread, and provide other, higher priority threads with an opportunity to use processing time. However, a high-priority thread will not be interrupted by lower priority threads, regardless of whether the high-priority thread uses more than the maximum amount of processing time. Under normal operation, most of the threads are inactive, and there is no conflict between threads for processing time; however, in those occasions where there is a conflict, this prioritized system allows the most important threads to continue uninterrupted where necessary. It should be noted, however, that even the highest priority thread (servo thread 254) occasionally returns time to the operating system (at those moments where an interruption can be tolerated), so that other threads are able to continue their operations even while the highest priority thread is active.

The threads operating in the CPU 52 generally fall into two categories: "communicating" threads which send information into and out of the powerpack 50, and "operating" threads which generate or process the information sent or received by the powerpack. There are two operating threads: state machine thread 246 and servo thread 254.

State machine thread 246 directs the console 30 to produce screen displays of the type shown in FIGS. 6A–6E, and also processes button presses by the user. Thread 246 is essentially a state machine, where each "state" corresponds to a display screen, and each operator keystroke produces a state transition. The software in program EPROM 58 (FIG. 3) essentially defines a state transition diagram, identifying specific states, displays associated with those states, and, for each state, the keystrokes or other activity which will cause a transition to another state.

Figure 7B:
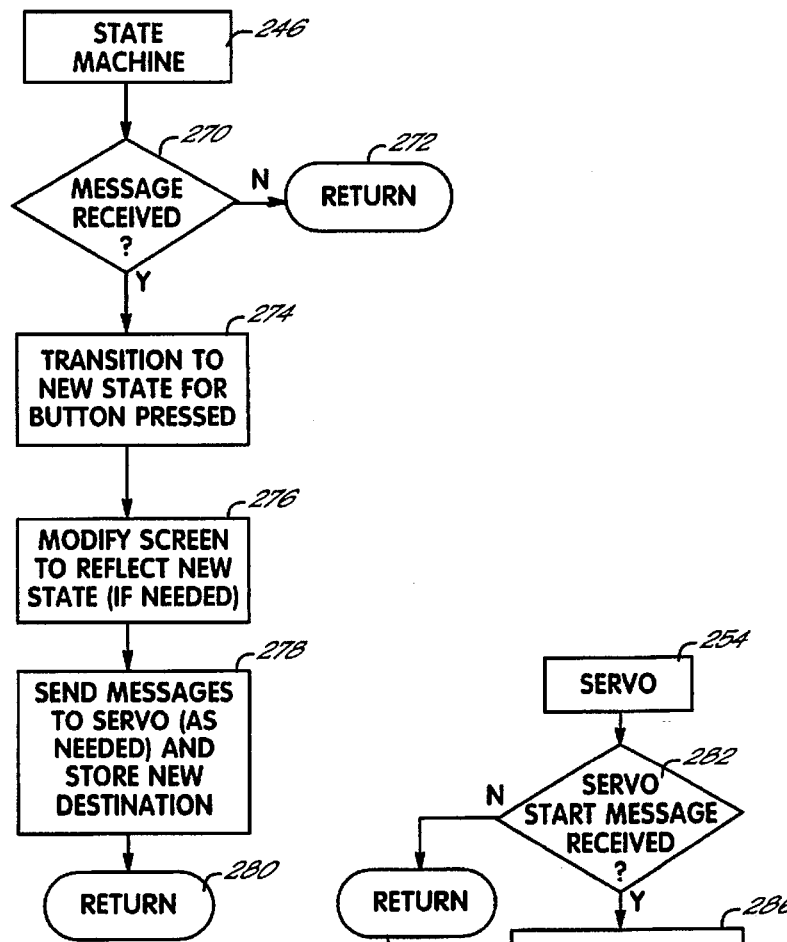

As shown in FIG. 7B, when initiated, thread 246 looks 270 for a message, for example a message from a communications thread indicating that console button was pressed, or a message from the servo thread indicating that the display should be updated to reflect recent injection activity. If no message has been received, the thread returns 272 time to the operating system. However, if a message has been received, the thread uses the software in program EPROM 58 to identify and transition 274 to the new state associated with the received keystroke or activity. In some cases, e.g. where the operator has pressed an invalid button, the new state will be the same as the old state; in other cases, the new state will be a different state. If the new state is a different state, the state machine thread sends messages to the appropriate communication thread to modify 276 the screen to reflect the new state. In addition, the state machine thread may send 278 messages to the servo thread, e.g. to notify the servo thread that the operator has pressed a button which starts a protocol. When this is completed, the state machine returns 280 to the operating system.

When a start message is sent to the servo thread, the thread sending the message initiates one or more global variables to indicate the kind of movement requested. Eight global variables (variables managed by the operating system and accessible by all threads), organized into four pairs, are used for this purpose. Each pair of variables identifies a desired new position for the plunger and a speed at which the plunger should move to that position. Four protocol phases can be described by the four variable pairs, and thus may be executed in one message to the servo thread. Thus, when the state machine thread sends 278 a message to the servo thread, it computes one or more desired ending positions and speeds from the selected protocol, and places the computed values into global variables.

Figure 7C:
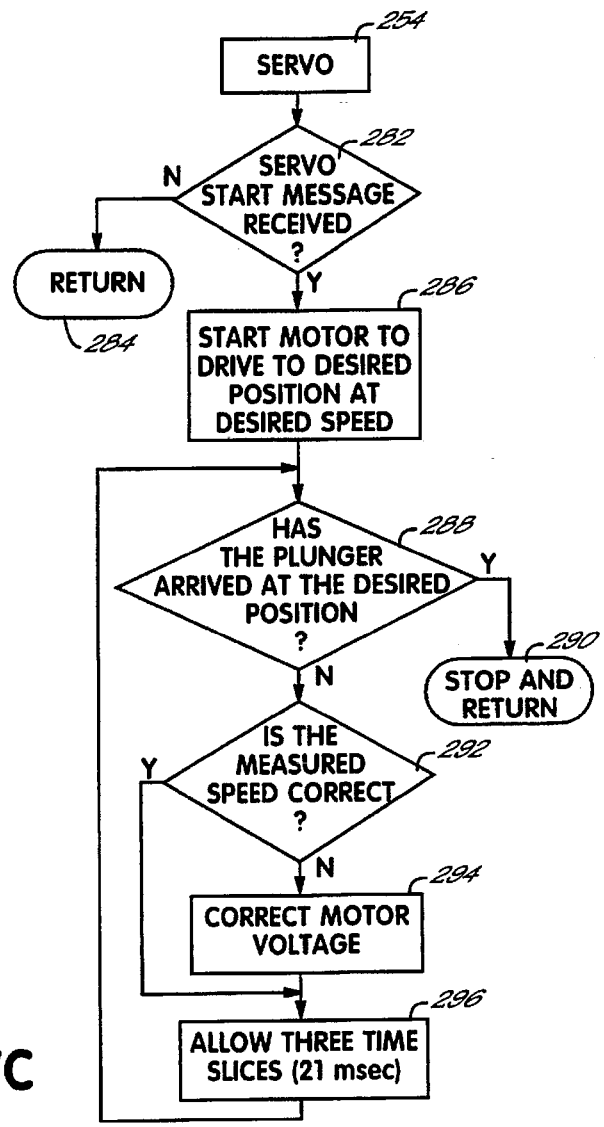

Referring to FIG. 7C, when initiated by the operating system, the servo thread 254 first checks 282 for a message telling the servo to start motion of the plunger. If no message is received, the servo thread returns 284 time to the operating system. If, however, a start message has been received, the servo thread starts 286 the motor to move to the desired position indicated by a global variable at the desired speed indicated by a global variable. At this point, the servo thread enters a loop; during each iteration the loop checks 288 if the plunger has arrived at the desired position (the plunger position is determined by the powerhead receive thread 260 as illustrated in FIG. 7E, below), and if so, the loop terminates and the servo thread stops 290 the motor and returns. However, if the plunger has not arrived at the desired position, the servo thread checks 292 if the speed of the motor is correct (the motor speed is measured by an interrupt routine illustrated in FIG. 7D, below). If the motor speed is incorrect, it is corrected 294 by adjusting the motor voltage. Once these steps are completed, the servo thread allows 296 the operating system three time slices (about 21 milliseconds) to operate other processes, after which it returns to step 288 to close the loop.

Figure 7D:
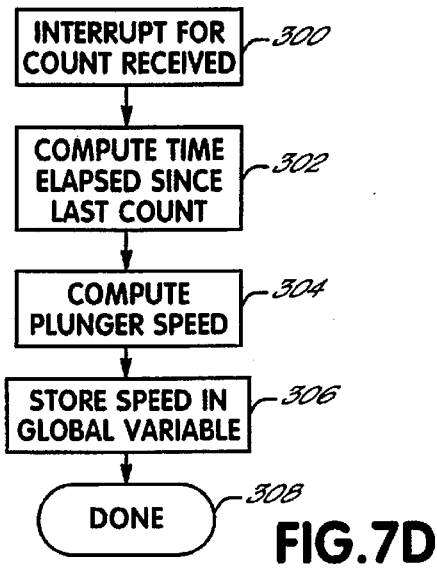
Figure 7E:
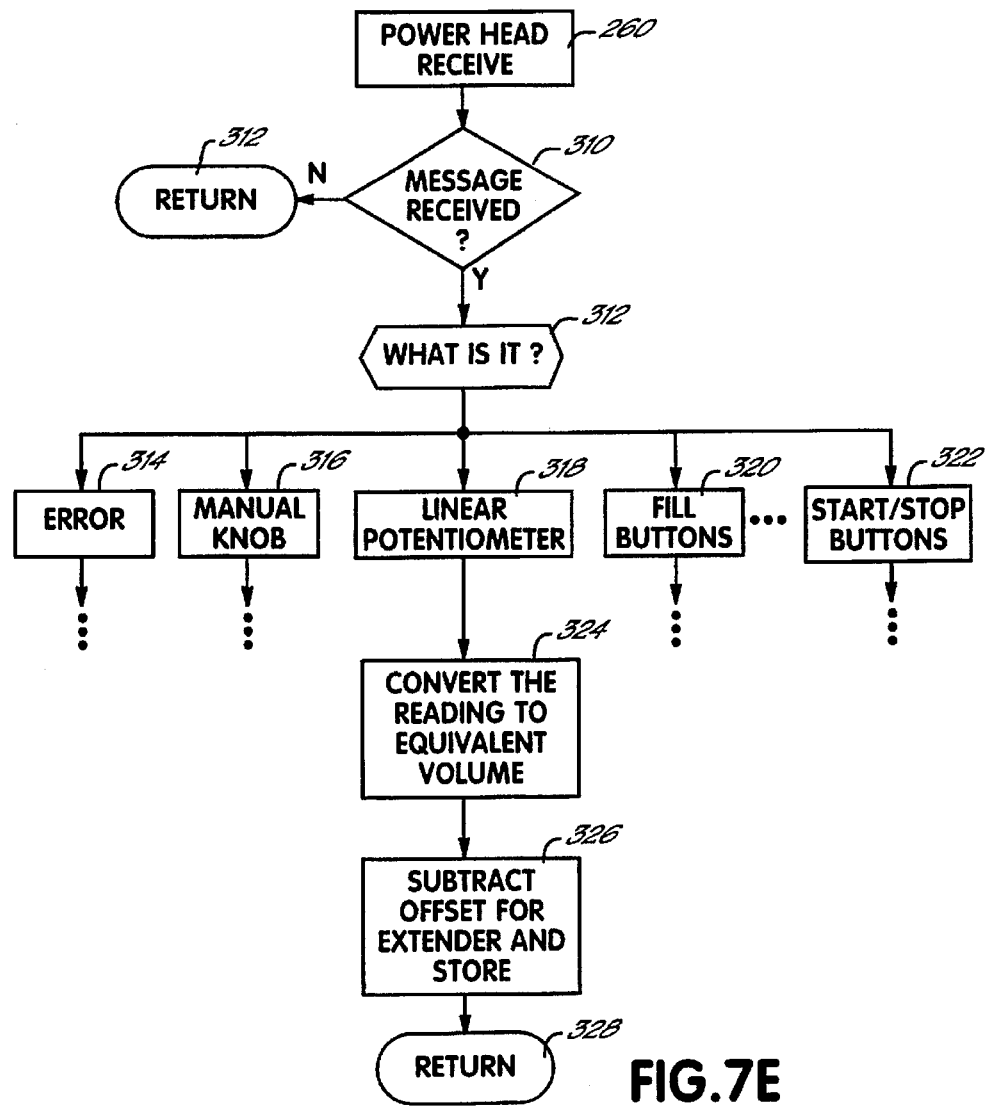

Referring to FIG. 7D, as noted above, the motor speed is measured by an interrupt routine. When a pulse is detected from the optical encoder 166 (FIG. 5) attached to the motor 98, the processor in the powerhead circuit board 160 causes an interrupt to travel on line 71 to CPU 52. When this interrupt is received 300, the interrupt routine computes 302 the time elapsed from the previous count interrupt, and from this elapsed time computes 304 the plunger speed. This speed value is stored 306 in a global variable (where it can be accessed by the servo routine), and the interrupt is done 308.

Referring to FIG. 7E, the powerhead receive thread 260 is responsible for receiving messages from the powerhead and performing a number of tasks in response, including relaying manual movements of the plunger to the servo thread and (as noted above) relaying position measurements to the servo thread during movement of the plunger.

When the operating system initiates 260 the powerhead thread, the thread first checks 310 for any messages; if none have been received, the thread returns 312 time to the operating system. However, if the thread has received a message, it determines 312 what the message is and acts appropriately (this determination is illustrated for clarity as a multi-way branch, but in the code in the fiche appendix it is implemented as a series of individual tests performed on in sequence). The message may contain an error message 314, a manual knob movement 316, a linear potentiometer reading 318 (which are periodically generated by the powerhead), a fill button reading 320 (which is periodically generated by the powerhead), a start/stop button press 322, or several others (multiple messages may be received at one time).

As shown in FIG. 7E, if the message contains a linear potentiometer reading 318, the reading is converted 324 into an equivalent volume (using calibration readings stored in EEPROM 62). Then, an offset value (which compensates for the presence of the extender in a partial pre-filled syringe), is subtracted 326 from the computed volume, and the result is stored in a global variable, where it can be later accessed by the servo thread at step 288 (FIG. 7C). The offset value used in step 326 is generated when the user identifies the partial pre-filled size in response to the display shown in FIG. 6F; if partial pre-filled syringes are not used, the offset is set to a constant zero value. Once the adjusted volume is stored, the powerhead thread returns 328 time to the operating system.

Figure 7F:
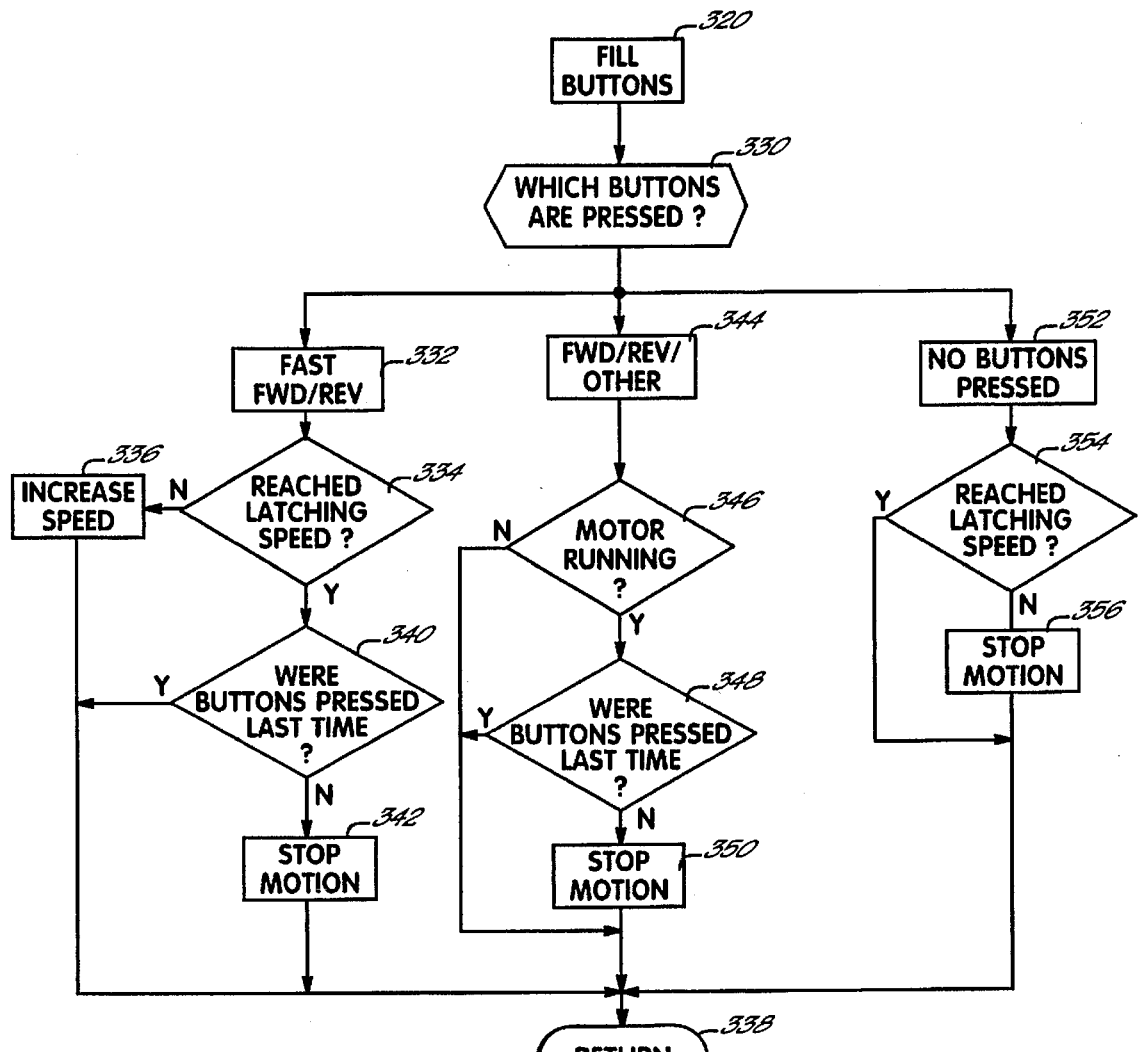

As shown in FIG. 7F, when a fill button reading is received (i.e., the received message indicates the state of buttons 46, 47 and 48 on the keyboard 162 of the powerhead), the powerhead thread first determines 330 which button, or buttons, are pressed.

If a "fast" button 48 and the forward button 46 or reverse button 47 are pressed 332, the thread first determines 334 whether the motor is at its maximum, latching speed (by reading the global variable indicating the motor speed, as produced by the interrupt routine illustrated in FIG. 7D). If not, the thread increases 336 the motor speed in the indicated direction—by increasing the value of the global variable identifying the desired speed, setting the global variable identifying the desired location to identify the end of the syringe (and sending a start servo message to the servo thread if the motor is not already running)—and returns 338 time to the operating system. If, however, the motor has reached its latching speed, then the thread determines 340 if buttons were pressed the last time a fill button reading was processed. If so, then the operator has accelerated the motor to its maximum speed and is continuing to hold down the buttons. In this situation, the motor should continue running at its maximum speed; therefore, the thread simply returns 338 time to the operating system. If, however, buttons were not pressed last time, then the operator latched the motor at maximum speed, released the buttons, and some time later pressed a button in an attempt to stop the motor. Thus, in this situation, the thread stops 342 the motor (by setting the global variable indicating the desired speed to zero), and returns 338 time to the operating system.

If the operator is pressing 344 the forward or reverse buttons alone, or any other combination of buttons, the thread first determines 346 if the motor is running (by checking the value of the global variable indicating the motor speed). If the motor not running, then a single keystroke will not start it running, so the thread simply returns 338 to the operating system. If, however, the motor is running, then the thread determines 348 if buttons were pressed the last time a fill button reading was processed. If buttons were pressed last time, then the operator is merely trying to keep the motor running at its current speed by holding a button down; therefore, in this situation, the thread simply returns 338 to the operating system, allowing the motor to continue running. If, however, buttons were not pressed last time, then the operator latched the motor at maximum speed, released the buttons, and some time later pressed a button in an attempt to stop the motor. Thus, in this situation, the thread stops 342 the motor (by setting the global variable indicating the desired speed to zero), and returns 338 time to the operating system.

If no buttons are pressed 352, the thread simply determines 354 if the motor is at its latching speed. If not, the thread stops 356 the motor and returns time to the operating system. Otherwise, the thread returns 338 directly, allowing the motor to continue running at the latching speed.

Figure 7G:
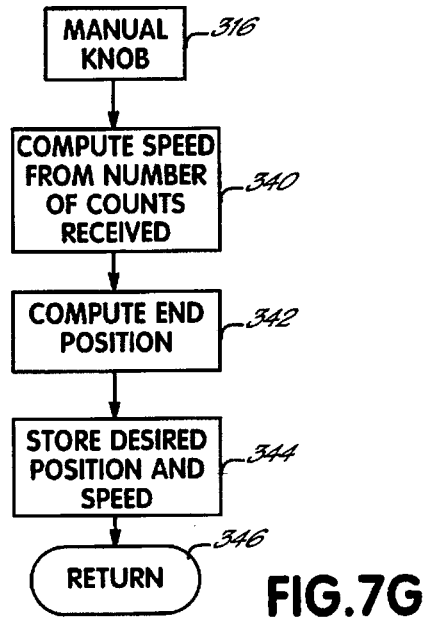

Referring to FIG. 7G, manual motion can also be created by turning the manual knob 163 (FIG. 5) mounted on the rear of the powerhead. As noted above, the powerhead CPU 160 regularly reports movements of the manual knob to the powerpack CPU 52. This report identifies the direction of rotation and the number of electrical pulses received from the knob since the last report (more pulses indicating greater speed of rotation). When a manual knob message is received 316, the powerhead receive thread first computes 340 a desired plunger speed from the number of pulses identified in the message, and computes 342 a desired end position from the number of pulses and the direction of rotation of the knob. These are then stored 344 in global variables accessible to the servo thread as described above. If the motor is not already running, the powerhead receive thread also sends a servo start message to the servo thread. Then the thread returns 346 time to the operating system.

The invention has been described with reference to a specific embodiment. However, it will now be understood that various modifications and alterations can be made to this specific embodiment without departing from the inventive concepts embodied therein. For example, the manual motion knob 163 may be replaced by any other control which allows velocity and direction control, for example by a button or knob which can be rotated or rocked to multiple positions corresponding to various velocities and directions of motions, or a set of buttons or knobs which allow the operator to separately select a desired velocity with one button or knob and a desired direction with another button or knob. Therefore, this specific embodiment is to be interpreted as exemplary and not limiting, with the scope of protection being determined solely from the following claims.

What is claimed is:

1. An injector of the type having a motor which advances and retracts a plunger located within a syringe toward and away from a nozzle located in the front of the syringe to inject fluid into or out of an animal subject, adapted for use with a syringe including an extender attached to said plunger, comprising:

a control circuit which causes said motor to move, said control circuit tracking the location of said motor while moving said motor, and a memory storing an offset value representative of the length of the extender which is attached to said plunger, wherein said control circuit computes a value indicative of the location of said plunger within said syringe by relating said stored offset value to the tracked location of said motor, and ceases motion of said plunger when said computed value indicates that said plunger is at an end of said syringe.

2. The injector of claim 1 further comprising
   a display, and
   a keypad usable by an operator to control said injector, wherein said control circuit generates and stores said offset value by controlling said display to request, from an operator, information sufficient to compute the length of the extender which is attached to said plunger, monitoring keystrokes on said keypad to determine said information, deriving said offset value therefrom, and storing the derived offset value in said memory.

3. The injector of claim 1 further comprising
   a detector located proximate to said syringe for detecting the length of the extender which is attached to said plunger from physical indicia on the syringe or extender and generating an electrical signal representative of the detected length, wherein said control circuit is responsive to said electrical signal, and generates and stores an offset value corresponding to the detected length represented by said electrical signal.

4. A method of controlling an injector of the type having a motor which advances and retracts a plunger located within a syringe toward and away from a nozzle located in the front of the syringe to inject fluid into or out of an animal subject, adapted for use with a syringe including an extender attached to said plunger, comprising:

storing an offset value representative of the length of the extender which is attached to said plunger, causing said motor to move, tracking the location of said motor while moving said motor, computing a value indicative of the location of said plunger within said syringe by relating said stored offset value to the tracked location of said motor, and ceasing motion of said plunger when said computed value indicates that said plunger is at an end of said syringe.

5. The method of claim 4 further comprising
   requesting, from an operator, information sufficient to compute the length of the extender which is attached to said plunger, and
   deriving said offset value from said information from said operator.

6. The method of claim 4 further comprising
   detecting the length of the extender which is attached to said plunger from physical indicia on the syringe or extender and generating an electrical signal representative of the detected length, and
   deriving said offset value from the detected length represented by said electrical signal.

7. An injector of the type having a motor which advances and retracts a plunger located within a syringe toward and away from a nozzle located at a distal end of the syringe to inject fluid into or out of an animal subject, adapted for use with syringe assemblies which have differing capacities, comprising:

a detector located proximate to a syringe installed on said injector for detecting a physical indicia on said syringe related to the capacity of said syringe, and generating an electrical signal representative of said physical indicia, and a control circuit which causes said motor to move and tracks the location of said motor while moving said motor, wherein said control circuit computes the location of a plunger within said syringe relative to an end of said syringe, by relating said electrical signal to the tracked location of said motor.

8. The injector of claim 7 wherein said control circuit ceases motion of said motor and plunger when a location of said plunger computed by said control circuit indicates that said plunger has arrived at an end of said syringe.

9. The injector of claim 7 wherein said electrical signal represents the length of an extender which is attached to said plunger within said syringe.

10. A method of controlling an injector of the type having a motor which advances and retracts a plunger located within a syringe toward and away from a nozzle located at an end of the syringe to inject fluid into or out of an animal subject, adapted for use with syringe assemblies which have differing capacities, comprising:

detecting a physical indicia on a syringe installed on said injector, said indicia being related to the capacity of said syringe, and generating an electrical signal representative of said physical indicia, causing said motor to move, tracking the location of said motor while moving said motor, and computing the location of a plunger within said syringe relative to an end of said syringe by relating said electrical signal to the tracked location of said motor.

11. The method of claim 10 further comprising:

ceasing motion of said plunger when a computed location of said plunger indicates that said plunger has arrived at an end of said syringe.

12. The method of claim 10 wherein said electrical signal represents the length of an extender which is attached to said plunger.

* * * * *